(12) United States Patent
Detalle et al.

(10) Patent No.: US 6,661,511 B2
(45) Date of Patent: Dec. 9, 2003

(54) METHOD AND APPARATUS FOR ENHANCED LASER-INDUCED PLASMA SPECTROSCOPY USING MIXED-WAVELENGTH LASER PULSES

(75) Inventors: Vincent Detalle, Montreal (CA); Louis St-Onge, Cote St-Luc (CA); Mohamad Sabsabi, Boucherville (CA)

(73) Assignee: National Research Council of Canada, Ottawa (CA)

( * ) Notice: Subject to any disclaimer, the term of this patent is extended or adjusted under 35 U.S.C. 154(b) by 2 days.

(21) Appl. No.: 10/046,227

(22) Filed: Jan. 16, 2002

(65) Prior Publication Data

US 2002/0093653 A1 Jul. 18, 2002

Related U.S. Application Data

(60) Provisional application No. 60/261,183, filed on Jan. 16, 2001.

(51) Int. Cl.[7] .............................................. G01N 21/63
(52) U.S. Cl. ...................................................... 356/318
(58) Field of Search .................................. 356/317, 318

(56) References Cited

U.S. PATENT DOCUMENTS

| | | | |
|---|---|---|---|
| 4,645,342 A | 2/1987 | Tanimoto et al. | 356/318 |
| 4,925,307 A | 5/1990 | Cremers et al. | 356/318 |
| 5,379,103 A | 1/1995 | Zigler | 356/73 |
| 5,757,484 A | 5/1998 | Miles et al. | 356/318 |
| 5,847,825 A | 12/1998 | Alexander | 356/318 |
| 5,946,141 A | * 8/1999 | Harrigan | 359/642 |
| 6,008,897 A | 12/1999 | Sabsabi et al. | 356/318 |

FOREIGN PATENT DOCUMENTS

| | | | |
|---|---|---|---|
| DE | 3836525 A1 | * | 5/1990 |
| GB | 2175737 A | * | 12/1986 |
| JP | 62085847 A | | 4/1987 |
| JP | 62188919 A | | 8/1987 |
| JP | 01321340 A | | 12/1989 |
| JP | 06241999 A | | 9/1994 |

* cited by examiner

Primary Examiner—F. L. Evans
(74) Attorney, Agent, or Firm—Marks & Clerk

(57) ABSTRACT

A sample of heterogeneous material is analyzed by directing a mixed-wavelength laser pulse at the sample to produce a plasma. The mixed wavelength pulse contains both shorter and longer wavelength components. The composition of the material is determined from the emission spectrum of the plasma.

18 Claims, 3 Drawing Sheets

METHOD AND APPARATUS FOR ENHANCED LASER-INDUCED PLASMA SPECTROSCOPY USING MIXED-WAVELENGTH LASER PULSES

CROSS-REFERENCE TO RELATED APPLICATION

This application claims the benefit under 35 USC 119(e) of U.S. provisional application No. 60/261,183 filed on Jan. 16, 2001.

BACKGROUND OF THE INVENTION

1. Field of the Invention

This invention relates to the field materials analysis, and in particular to a transient, rapid spectroscopic method for the analysis of unknown heterogeneous materials by enhanced mixed-wavelength laser plasma spectroscopy.

2. Description of Related Art

Most analytical techniques for the analysis of unknown heterogeneous materials used in industry require samples be taken to the laboratory, and analyzed by time consuming procedures involving instrumentation such as Auger and mass spectrometers, energy-dispersive spectrometry, liquid or gas chromatography, graphite furnace atomic absorption spectroscopy or inductively coupled plasma optical emission spectrometry. Faster in-situ methods such as spark-discharge optical spectrometry are only applicable to electrically conductive materials, while X-ray backscattering probes are limited in sensitivity.

An emerging method, known as laser-induced plasma spectroscopy, promises to provide rapid, in-situ compositional analysis of a variety of materials in hostile environments and at a distance. Basically, this method involves focusing a high-power pulsed laser onto the material, thus vaporizing and ionizing a small volume of the material to produce a plasma having an elemental composition which is representative of the material composition. The optical emission of the plasma is analyzed with an optical spectrometer to obtain its atomic composition. This method has been applied to a variety of materials and industrial environments, as exemplified in the following documents.

U.S. Pat. No. 4,645,342 by Tanimoto et al. describes a probe for spectroscopic analysis of steel including focusing an infrared laser pulse on the steel material and collecting, at an angle of 16 degrees or more, the light emitted by the irradiated surface spot. This probe includes a single laser pulse at 1064 nm not collinear with the collecting optics.

U.S. Pat. No. 4,986,658 by Kim describes a probe for molten metal analysis by laser-induced plasma spectroscopy. The probe contains a high-power laser producing a pulse having a triangular waveshape. In this case, the vaporizing laser beam and collecting optics are collinear, but only a single laser pulse at 1064 nm is used to vaporize the molten metal surface.

U.S. Pat. No. 5,042,947 by Pötzschke et al. describes an application of laser-induced plasma spectroscopy for the sorting of solid metal particles, namely shredder scrap from automotive recycling processes. A single laser pulse at 1064 nm is used to produce each laser spark.

U.S. Pat. No. 5,379,103 by Zigler describes a mobile laboratory for in-situ detection of organic and heavy metal pollutants in ground water. Pulsed laser energy is delivered via fiber optic media to create a laser spark on a remotely located analysis sample. The system operates in two modes, one is based on laser-induced plasma spectroscopy and the other on laser-induced fluorescence. Again, only single laser pulses at 1064 nm are used to analyze pollutants in ground water.

U.S. Pat. No. 5,847,825 by Alexander discloses a LIBS system using a femtosecond laser pulse for plasma generation. U.S. Pat. No. 5,757,484 by Miles et al. describes a subsurface soil contaminant identification system using a cone penetrometer based on laser-induced breakdown spectrometry.

In all of the above patents, single laser pulses based on one wavelength are used to vaporize, ionize and excite a portion of the material to be analyzed by laser-induced plasma emission spectroscopy.

The Japanese patent JP62-41999 by Yamamoto et al. discloses a spectral analytical method by laser emission using two step excitation methods. In this case, the second laser beam is perpendicular to the first laser beam and parallel to the target. The two pulses used are at the same wavelength and separated by a specific delay time. The JP62-41999 patent does not use multiple-wavelength laser pulses.

The Japanese patent JP62-85847 by Takaharu describes a method for direct emission spectrochemical analysis of laser multistage excitation. The laser pulse is divided into two pulses P and Q at the same wavelength by a beam splitter. The first pulse P converges on the sample to produce the plasma and then the second pulse Q delayed by an optical delay device converges on the plasma to enhance the light emission. Two pulses at the same wavelength separated with a specific time by an optical delay device generate the plasma on the sample.

In order to enhance sensitivity of laser-induced plasma spectroscopy; several patents, such as JP62-188919 and JP1-321340, generate the plasma by laser double pulse mode. Again, the two pulses are separated by a specific delay time and there is no mention of multiple wavelengths to generate the plasma.

Two temporally close sparks induced by two collinear lasers at 1064 nm are used by Cremers et al. in U.S. Pat. No. 4,925,307 for the spectrochemical analysis of liquids. The sparks occur in the volume of the liquid. The spark produced by the first laser pulse produces a bubble in the liquid which stays in the gaseous state for hundreds of microseconds after the first spark has decayed, so that the second laser pulse, fired typically 18 microseconds after the first pulse, produces a second spark within the gaseous bubble. The emission spectrum of the second spark is detected by a spectrometer oriented at 90 degrees from the laser beam axis. A much increased detectability of the atomic species is obtained by sampling the bubble with the second laser spark. The two laser pulses are at the same wavelength and separated by a time delay.

U.S. Pat. No. 6,008,897 by Sabsabi et al. discloses a method and apparatus for enhanced laser-induced plasma spectroscopy using two pulses of different wavelengths. The first laser pulse, for example in the ultraviolet, vaporizes a small volume at the surface of the material and produces a plasma which is subsequently enhanced by the second laser pulse, for example in the near-infrared. The two pulses are temporally spaced by a predetermined time period; they are not simultaneous as in the present invention.

All work related to laser-induced plasma spectroscopy in the literature uses a single-wavelength laser pulse or double laser pulses separated by a period of time.

SUMMARY OF THE INVENTION

According to the present invention there is provided a method of analyzing the composition of heterogeneous materials comprising providing a sample of a material to be analyzed; directing a mixed-wavelength laser pulse at said sample to produce a plasma; and determining the composition of said material from the emission spectrum of said plasma.

The invention provides a method and apparatus to enhance the analytical sensitivity of laser-induced plasma spectroscopy and to provide a reliable analysis of the surface of materials by using a mixed-wavelength laser pulse. In conventional laser-induced plasma spectroscopy, the plasma is produced by a single laser pulse or double pulses separated by a given period of time. A shorter wavelength laser pulse is better absorbed by the sample than a longer wavelength laser pulse, while the longer wavelength pulse is efficiently absorbed by the plasma. In particular, a longer wavelength pulse is absorbed by the portion of the plasma spark which faces the incoming laser beam. In the present invention, a mixed-wavelength laser pulse produces the plasma. The shorter wavelength component of the laser pulse ablates efficiently the sample and rapidly produces an initial plume of ablated matter containing seed electrons. The longer wavelength component of the laser pulse is then well absorbed in the initial plume and further ionizes the ablated matter, rapidly producing a plasma sufficiently dense to prevent the laser from reaching the material surface. Thereafter, the shorter wavelength component of the laser pulse warms up the part of the plasma closest to the sample because the outer portion of the plasma is less absorbing at this wavelength. Meanwhile, the portion of the plasma spark which faces the incoming laser beam absorbs the longer wavelength component of the laser pulse whose wavelength is efficiently absorbed by the plasma. The result is a plasma spark of high, uniform and sustained temperature and emissivity, enabling one to record a plasma emission signal which is orders of magnitude stronger than what would be obtained with a single laser pulse of similar energy. This can be achieved by combining two simultaneous pulses from separate lasers.

Maintaining alignment of the two focal spots can be difficult, and drift in this alignment can significantly affect emission signals and efficiency of sensitivity enhancement. Another aspect of the present invention is the production of mixed-wavelength pulses with a single laser that is provided with one or several frequency conversion devices such as frequency doubling crystals or optical parametric oscillators. There are several advantages of using a single laser. This includes a more compact, reliable, and less expensive system than can be achieved using two lasers. Moreover, no alignment of two laser beams on the sample is required; the wavelength combination is fixed and assured.

The invention also provides an apparatus for use in the analysis of heterogeneous materials comprising at least one laser for generating a mixed-wavelength pulsed laser beam; and a focusing arrangement for focusing said mixed wavelength laser beam onto a sample to produce a plasma.

In one embodiment two the outputs of two lasers operating at different wavelengths are combined. In another embodiment the output of a single laser is split into separate beams. After the frequency of one of the separate beams has been changed, they are again combined into a single mixed wavelength beam.

In a still further embodiment, a frequency converter is included in the output beam of a single laser so as to generate at least one new frequency while retaining the original frequency so as to produce the mixed wavelength beam.

BRIEF DESCRIPTION OF THE DRAWINGS

The invention will now be described in more detail, by way of example only, with reference to the accompanying drawings, in which.

DETAILED DESCRIPTION OF THE INVENTION

In laser spectroscopy, bursts containing two laser pulses separated by a given time delay have been shown to enhance the light emission from laser-produced plasmas, compared to single pulses of the same energy. This technique directly improves the sensitivity of laser-induced plasma spectroscopy when analysing trace or minor elements in a given sample. The pulses in a burst can be of equal or different wavelength.

The reason for the enhancement is that the second laser pulse is able to reheat the whole volume of the plume of ablated matter left after the first pulse. A time delay is required between the pulses in order for the first plasma to lose some of its ionization so that the second pulse can penetrate into and reheat the core of the plume where most of the analyte is found instead of being absorbed mainly at the periphery of a very dense plasma.

Figure 1:
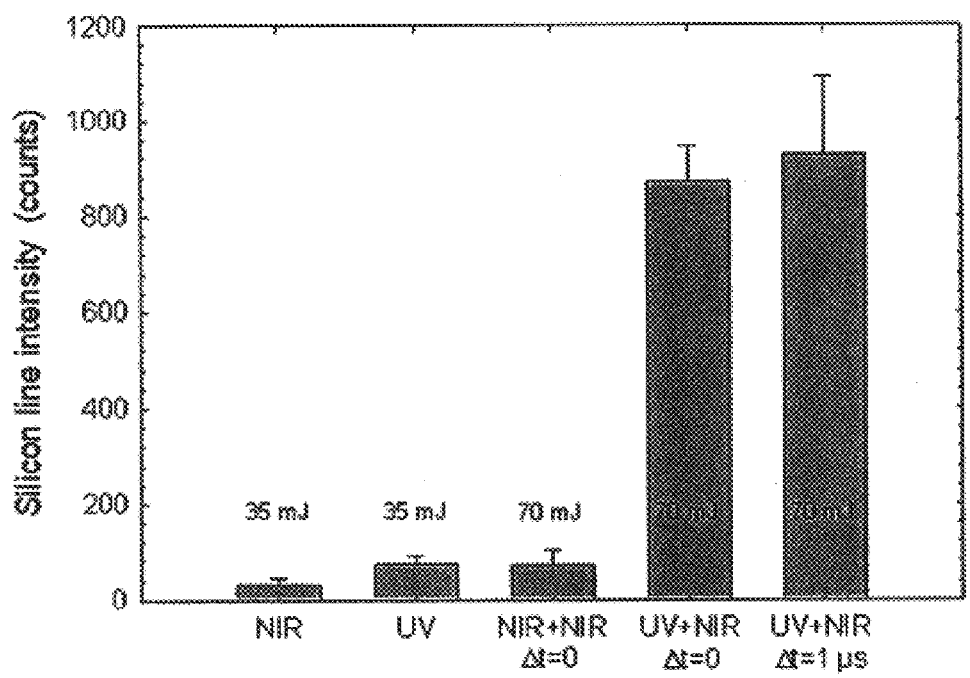
FIG. 1 is a chart showing the peak intensity of the Si I 288.16 nm line for different laser pulse combinations. The total laser energy is given in each case. The value of $\Delta t$ indicates the time delay between two laser pulses. The measurement is made 2 $\mu$s after a single pulse or the second pulse of a burst, and the signal is integrated during 0.25 $\mu$s. The values given are the average of 20 measurements. The standard deviation is given by the error bar.

In can be shown, unexpectedly, that using the fundamental (1064 nm) and fourth harmonic (266 nm) of Nd:YAG lasers there is a significant intensity enhancement even when two pulses of different wavelengths are fired simultaneously on the sample. This is illustrated in FIG. 1, which shows the peak intensity of a spectral line of neutral silicon with different combinations of laser pulses (silicon was present in 0.25% concentration in an aluminum alloy sample). When two near-infrared (NIR) pulses of 35 mJ each are fired simultaneously, the resulting line intensity is about twice that obtained with a single NIR pulse. This does not constitute an enhancement in itself because the total laser energy has also doubled. For individual ultraviolet (UV) and NIR pulses of 35 mJ each (at 266 nm and 1064 nm respectively), the line intensities are of the same order of magnitude. However, when both are fired simultaneously, the resulting intensity is much larger than for the individual pulses, and is of the same magnitude as when there is a time delay between the pulses (e.g. 1 μs). This increase cannot be explained by the doubling of energy; it constitutes a true enhancement. For example, compared to a single 35 mJ NIR pulse, the mixed 70 mJ UV-NIR pulse causes a factor of 30–40 enhancement of the silicon line. Compared to a single 70 mJ NIR pulse, the enhancement would in the order of a factor 15–20.

Figure 2:
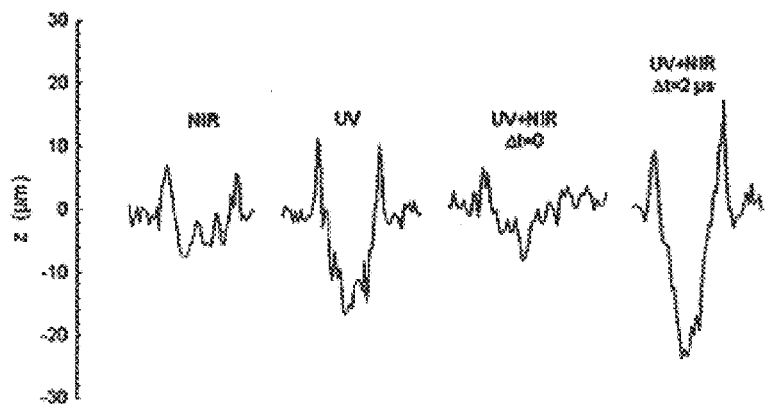
FIG. 2 shows the crater cross-section for different laser pulse combinations. The profile is obtained by optical coherence tomography. The craters each result from 25 successive laser shots or bursts. The value of $\Delta t$ indicates the time delay between two laser pulses.

Since the mass yield of laser ablation is generally larger when shorter laser wavelengths are used, it might be thought that the observed intensity enhancement with a mixed UV-NIR pulse could have been explained by enhanced ablation. However, this is not the case. FIG. 2 shows the crater profile resulting from 25 laser shots in different laser pulse combinations, as measured with optical coherence tomography. For the same laser energy, a UV pulse ablates more than a NIR pulse. When both are fired in succession with a delay of, say 2 μs, the crater depth is approximately the sum of that for the individual pulses. However, when both pulses are fired simultaneously, the crater is very shallow.

It is believed that the reason why the surface is less affected is that plasma shielding occurs earlier in the pulse, reducing the amount of energy that reaches the surface (plasma shielding is the phenomenon whereby the laser is completely absorbed in, or reflected by, the plasma on its way to the surface). In any case, the mixed 70 mJ UV-NIR pulse ablates much less than a single 35 mJ UV pulse (FIG. 2), but leads to a much larger signal (FIG. 1).

Figure 3:
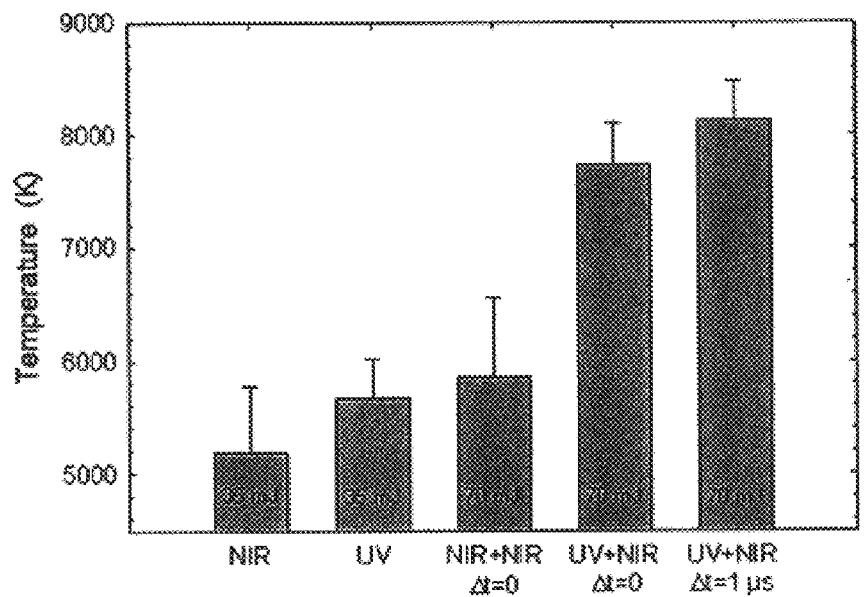
FIG. 3 shows the excitation temperature corresponding to different laser pulse combinations. This temperature is obtained by the Boltzmann plot method using nine iron lines. The total laser energy is given in each case. The value of $\Delta t$ indicates the time delay between two laser pulses. The measurement is made 2 $\mu$s after a single pulse or after the second pulse of a burst, and the signal is integrated during 0.5 $\mu$s. The values given are the average of 20 measurements. The standard deviation is given by the error bar.

The explanation for the large intensity enhancement obtained with the mixed UV-NIR pulse is found in a temperature enhancement. This is shown in FIG. 3. By comparing the results with FIG. 1, the correlation between the line intensities and the plasma temperature becomes clear; the silicon emission is greater because the silicon atoms in the vapor plume are more efficiently excited in a hotter plasma. The temperature obtained with the mixed 70 mJ UV-NIR pulse is more than 2000 K higher than for single (UV or NIR) 35 mJ pulses or even than for a 70 mJ NIR pulse. It is of the same order of magnitude as for UV and NIR pulses separated by 1 μs.

Figure 4:
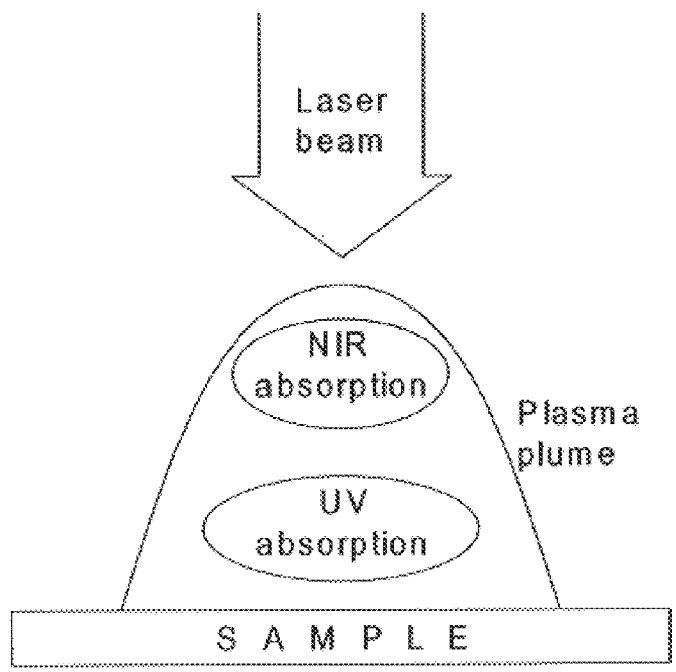
FIG. 4 is a schematic drawing of the laser-induced plasma plume, and of the regions where the different wavelength components of the mixed laser pulse are mostly absorbed.

It is believed that the enhancement obtained with the mixed UV-NIR pulse is due to the following events: (i) the UV component of the mixed pulse is well absorbed by the material and rapidly produces a vapor plume which comprises free electrons acting as seeds for further laser absorption; (ii) the NIR component of the mixed pulse is then well absorbed in this early plasma through the inverse bremsstrahlung process, and rapidly ionizes the vapor; (iii) afterwards, the UV component of the mixed pulse, because it is less well absorbed (than NIR radiation) in low-density regions at the plasma periphery, is able to penetrate deeper and efficiently heat the core of the plasma, where most of the ablated matter (including the silicon) is found, while the NIR component is mostly absorbed at the periphery. This is illustrated in FIG. 4. Steps (i) and ii) lead to an early plasma shielding, which explains the shallower craters, while step (iii), namely the absorption of the UV component in the core of the plume, leads to an efficient excitation of the ablated matter.

By combining different wavelengths in a same pulse, it is possible to achieve a temperature and intensity enhancement comparable to that obtained with the double (sequential) pulse approach, and probably for a similar reason: the whole volume of the plume (not just the periphery) is efficiently heated by laser radiation.

This invention is not limited to the particular combination of wavelengths given above (266 and 1064 nm). It is only required that the beam contains one or more long wavelengths that can induce an early plasma shielding, and one or more relatively shorter wavelengths that are at first well absorbed by the material (to vaporize it and produce seed electrons) and later absorbed deep in the plasma, in order to efficiently heat the core of ablated matter.

One possible embodiment of the present invention is that described above, in which two separate lasers operating at different wavelengths are fired simultaneously, and whose beams are combined colinearly on the sample. The apparatus in this case is the same as described in U.S. Pat. No. 6,008,897 by Sabsabi et al., the contents of which are herein incorporated by reference, with the exception of the fact that the time delay between the pulses from the two lasers is approximately zero.

Other embodiments of the present invention are possible, wherein a single laser is used instead of two separate lasers producing different wavelengths. There are two main approaches for producing mixed wavelength pulses with a single laser. These are described with reference to FIGS. 5 and 6.

Figure 5:
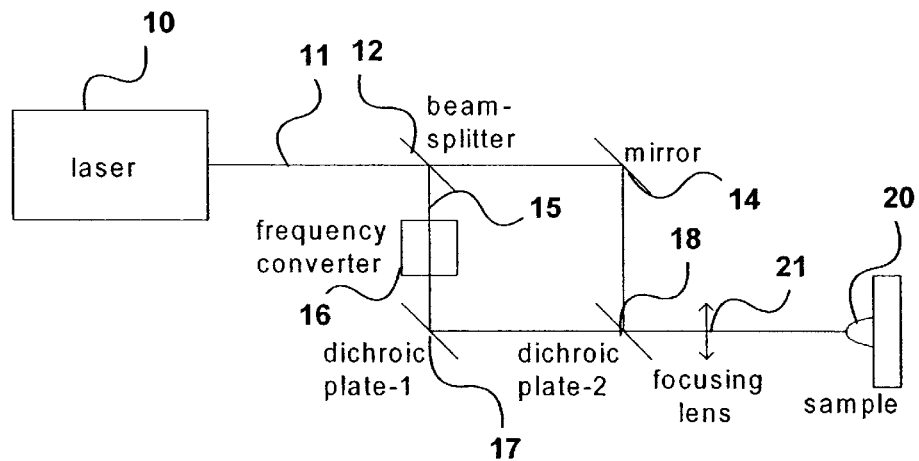
FIG. 5 is a block diagram showing the apparatus for producing mixed-wavelength laser pulses with a two-branch approach. The apparatus for collecting, spectrally resolving, and detecting the plasma emission is not shown.

The first approach, shown in FIG. 5. In this embodiment a laser 10 produces an output beam 11 which is separated into two branches 13, 15 using a beamsplitter 12. One of the branches 15 is passed through one or several frequency conversion devices 16 (frequency-doubling crystal or optical parametric oscillator for example) which produces a beam of different wavelength. The conversion device is followed by a dichroic plate 17 which reflects only the new wavelength. In the other branch, the laser wavelength is left unchanged (or may also be converted using additional frequency conversion devices). The two branches are then combined on the target 20 using a dichroic plate 18. An achromatic lens 21 should be used to focus the beam on the sample. Alternatively, separate focusing lenses can be placed in each branch prior to combining the beams. Because the path length is the same along the two branches, the pulses at the two different wavelengths arrive simultaneously on the sample. If the two beams are colinear, this is equivalent to firing a single pulse containing two wavelengths.

Figure 6:
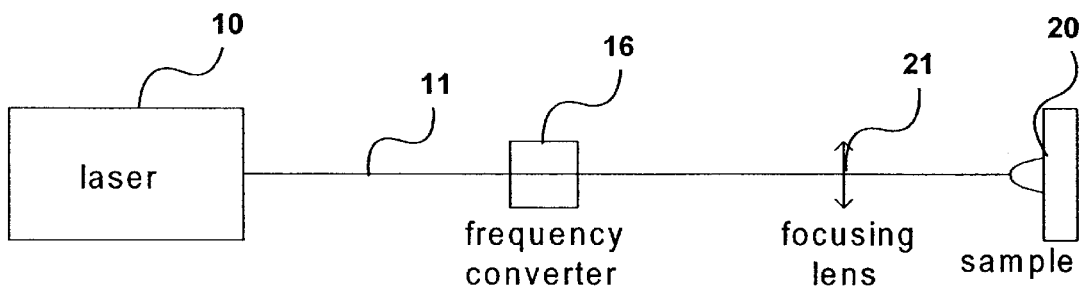
FIG. 6 is a block diagram showing the apparatus for producing mixed-wavelength laser pulses using the simpler single-branch approach. The apparatus for collecting, spectrally resolving, and detecting the plasma emission is not shown.

The second approach, shown in FIG. 6, is simpler and more practical. One or several frequency conversion devices 16 are placed directly at the exit of the laser, but all wavelengths are retained afterwards. An achromatic lens should be used to focus the beam on the sample. This embodiment does not involve the critical step of aligning two beams on the sample; a single mixed-wavelength beam is used.

As a specific example, one can use a single Nd:YAG laser at 1064 nm, followed by a frequency-doubling crystal to produce the second harmonic at 532 nm. This can then be followed by a second frequency-doubling crystal which produces the fourth harmonic at 266 nm. The mixed-wavelength beam therefore contains three wavelengths: 1064, 532, and 266 nm.

However, the present invention is not limited to such a wavelength combination. Any type of laser followed by one or several frequency conversion devices could be used to produce a mixed-wavelength beam, containing both relatively short and relatively long wavelengths.

Although the invention has been described and illustrated in detail, it is clearly understood that the same is by way of illustration and example only and is not to be taken by way of limitation, the spirit and scope of the present invention being limited only by the terms of the appended claims.

We claim:

1. A method of analyzing the composition of heterogeneous materials comprising:

providing a sample of a material to be analyzed;

directing a mixed-wavelength laser pulse at said sample to produce a plasma; and determining the composition of said material from the emission spectrum of said plasma.

2. A method as claimed claim 1, wherein said mixed wavelength pulse comprises a shorter wavelength component that ablates efficiently the sample and rapidly produces an initial plume of ablated matter containing seed electrons and a longer wavelength component that is absorbed in said initial plume and further ionizes the ablated matter, rapidly producing a plasma sufficiently dense to prevent the laser from reaching the material surface.

3. A method as claimed in claim 1, wherein said mixed wavelength pulse is formed by combining two simultaneous pulses from separate lasers.

4. A method as claimed in claim 1, wherein said mixed wavelength pulse is formed with a single laser that is provided with one or more frequency conversion devices.

5. A method as claimed in claim 4, wherein said one or more frequency conversion devices generates one or more harmonics of the output of said single laser.

6. A method as claimed in claim 4, wherein said frequency conversion devices are selected from the group consisting of: frequency doubling crystals and optical parametric oscillators.

7. A method as claimed in claim 1, wherein said mixed wavelength pulse comprises an infrared component and an ultraviolet component.

8. A method as claimed in claim 7, wherein said infrared component is a near infrared component.

9. A method of analyzing the composition of heterogeneous materials comprising:

providing a sample of a material to be analyzed;

directing a mixed-wavelength laser pulse having one or more relatively shorter wavelength components that are initially well absorbed by the material to vaporize the material into a plasma and produce seed electrons and one or more relatively longer wavelength components that are absorbed in said plasma and induce plasma shielding; and determining the composition of said material from the emission spectrum of said plasma.

10. A method as claimed in claim 9, wherein said one or more shorter wavelength components are ultraviolet and said one or more longer wavelength components are infrared.

11. A method as claimed in claim 9, wherein said wavelength components include a wavelength at 1064 nm and one or more harmonics thereof.

12. An apparatus for use in the analysis of heterogeneous materials comprising:

at least one laser for generating a mixed-wavelength pulsed laser beam; and a focusing arrangement for focusing said mixed wavelength laser beam onto a sample to produce a plasma; and a spectrum analyzer determining the composition of said material from the emission spectrum of said sample.

13. An apparatus as claimed in claim 12, comprising two said lasers operating at different wavelengths and arranged to be tired simultaneously, and a combiner for combining beams from said respective lasers into a single mixed wavelength output beam that is focused onto said sample.

14. An apparatus as claimed in claim 12, comprising a single said laser producing an output beam; a beam splitter for separating said output beam into separate beam portions; a frequency converter for changing the frequency of at least one of said separate beam portions; and a combiner for combining the separate beam portions into a single mixed wavelength beam that is focused onto the sample.

15. An apparatus as claimed in claim 12, comprising a single said laser producing an output laser beam; a frequency converter for generating at least one new frequency in the laser beam while retaining the original frequency so as to produce said mixed wavelength beam that is focused onto the sample.

16. An apparatus as claimed in claim 12, wherein said focusing arrangement is an achromatic lens.

17. An apparatus as claimed in claim 15, wherein said laser is a Nd:YAG laser operating at 1064 nm.

18. An apparatus as claimed in claim 15, wherein said frequency converter generates harmonics of said output beam produced by said laser.

* * * * *